(12) United States Patent
Rebeski et al.

(10) Patent No.: US 7,642,088 B2
(45) Date of Patent: Jan. 5, 2010

(54) DEVICE FOR SUSCEPTIBILITY TESTING OF BACTERIAL PATHOGENS AND VACCINE STRAINS IN POULTRY

(75) Inventors: Dierk E. Rebeski, Cuxhaven (DE); Ilka Schroder, Nordleda (DE); Michael Iburg, Bremen (DE)

(73) Assignee: Lohmann Animal Health GmbH & Co. KG, Cuxhaven (DE)

( * ) Notice: Subject to any disclaimer, the term of this patent is extended or adjusted under 35 U.S.C. 154(b) by 389 days.

(21) Appl. No.: 11/096,904

(22) Filed: Apr. 1, 2005

(65) Prior Publication Data

US 2005/0282243 A1   Dec. 22, 2005

(30) Foreign Application Priority Data

Apr. 19, 2004   (DE) .................. 20 2004 006 282 U

(51) Int. Cl.
  C12M 1/34 (2006.01)
  C12M 3/00 (2006.01)
  C12Q 1/68 (2006.01)
(52) U.S. Cl. .................. 435/288.4; 435/6; 435/288.5
(58) Field of Classification Search .............. 435/288.5, 435/6
See application file for complete search history.

(56) References Cited

U.S. PATENT DOCUMENTS

| | | | | |
|---|---|---|---|---|
| 4,101,383 A * | 7/1978 | Wyatt et al. | ..................... | 435/5 |
| 4,448,534 A * | 5/1984 | Wertz et al. | .................. | 356/435 |
| 4,778,758 A * | 10/1988 | Ericsson et al. | ................ | 435/32 |
| 5,026,638 A * | 6/1991 | Saperstein | .................... | 435/32 |
| 5,789,173 A * | 8/1998 | Peck et al. | ...................... | 435/6 |
| 5,976,828 A * | 11/1999 | Timberlake et al. | ........... | 435/34 |
| 6,083,500 A * | 7/2000 | Wooley et al. | ........... | 424/93.48 |
| 6,265,182 B1 * | 7/2001 | Kocagoz | ...................... | 435/32 |
| 6,479,056 B1 * | 11/2002 | Linde et al. | .............. | 424/258.1 |
| 2003/0134779 A1 * | 7/2003 | Diarra et al. | ................... | 514/6 |

FOREIGN PATENT DOCUMENTS

EP   0 263 528 B1   10/1987
EP   0 642 796 B1   9/1993

* cited by examiner

*Primary Examiner*—Walter D Griffin
*Assistant Examiner*—Lydia Edwards
(74) *Attorney, Agent, or Firm*—Vidas, Arrett & Steinkraus, P.A.

(57) ABSTRACT

Device for susceptibility testing of bacterial pathogens and vaccine strains in poultry with a microtiter plate comprising a plurality of wells and at least one well with a coating containing an antibiotic of a marker of a vaccine strain for the vaccination of poultry.

18 Claims, 4 Drawing Sheets

DEVICE FOR SUSCEPTIBILITY TESTING OF BACTERIAL PATHOGENS AND VACCINE STRAINS IN POULTRY

CROSS-REFERENCE TO RELATED APPLICATIONS not applicable.

STATEMENT REGARDING FEDERALLY SPONSORED RESEARCH not applicable.

BACKGROUND OF THE INVENTION

The invention relates to a device for susceptibility testing of bacterial pathogens and vaccine strains in poultry, in particular chickens, turkeys and ducks.

Two methods are available to the microbiological laboratory for in-vitro susceptibility testing of bacterial pathogens: the diffusion method and the dilution method. The most frequently used diffusion method is the disc agar diffusion method. The resistance test is carried out on a solid medium and the inhibition zone diameter (IZD) is evaluated for a constant concentration of the active substance absorbed in the disc. The inhibition zone diameter breakpoints can be associated with the categories 'susceptible', 'intermediate' and 'resistant'.

Also based on the diffusion method, the E-test combines the use of a solid medium with a gradient of the active substance on a paper strip. The formation of an elliptical zone of inhibition allows the minimum inhibitory concentration (MIC) to be determined.

In the dilution method the growth of test bacteria in a liquid medium is tested in the series dilution test in the presence of different concentrations of the active substance. The susceptibility of the pathogen relative to the different concentrations of active substance is analysed by determining the MIC (primary method). For human medicine diagnosis the series dilution test has been established as the standard method of investigation for a high sample throughput. In diagnostic veterinary medicine this is preferably used for bacterial pathogens isolated from pigs and cattle, in order to establish the current resistance situation of bacterial pathogens in livestock. The quantitive method also assists the vet in the choice of active substance and therefore the success of the treatment.

Methods which can be standardised and automated are thus available for susceptibility testing of bacterial pathogens in poultry. There are however no corresponding methods for discriminating and determining field strains and vaccine strains in poultry. Moreover, this is not in combination with an antibiogram.

From this, the object of the invention is to provide a device for susceptibility testing of bacterial pathogens and vaccine strains in poultry which can be standardised and automated.

The device according to the invention for the susceptibility testing of bacterial pathogens and vaccine strains in poultry has a microtiter plate comprising a plurality of wells with at least one well with a coating containing an antibiotic of a marker of a vaccine strain for the vaccination of poultry.

The coating present in at least one well of the microtiter plate allows discrimination between a pathogenic field strain of a bacterial pathogen and the vaccine strain cultivated for vaccination which can be discriminated from the field strain. The discrimination is based on the fact that the vaccine strain comprises a marker which is accompanied by increased resistance or increased susceptibility of the vaccine strain towards an antibiotic. The coating is in the solid state and is applied in a manner known to the person skilled in the art. If a bacterial pure culture in suspension in a suitable nutritive solution is dispensed into a well comprising a coating containing the antibiotic, the antibiotics are thus rehydrated and regain their full effectiveness. After incubation (for example at 35 to 37° C. for 18 to 24 hours) the growth of the bacteria can be measured. Using the growth of the bacteria it can be determined whether it is a pathogen or a vaccine strain. The growth of resistant vaccine strains is not affected by the coating, namely in comparison with field strains. The growth of susceptible vaccine strains, however, is affected by the coating compared to that of field strains. Bacterial growth is indicated by increasing turbidity of the suspension. This can be measured visually or objectively by means of a photometer with no room for interpretation by the user. This allows the uptake of vaccines by poultry to be monitored and field strains to be combatted by a standardised test. The device can also be used for automatic processing.

According to an embodiment at least one well comprises a coating containing an antibiotic of a marker of a *salmonella* vaccine strain. It refers for example to antibiotics which are markers of *salmonella* metabolic drift mutants or vaccine strains. Furthermore, it refers, for example, to specific antibiotics which have increased susceptibility to the *salmonella* vaccine strain due to an envelope marker. Similar *salmonella* vaccine strains are revealed in the European Patent EP 0 263 528 B1 (in particular in the claims and in the tables in lines 26 to 49 of page 5) and in the European Patent EP 0 642 796 B1 (in particular in the claims and the tables on page 6, lines 30 to 46). The publication of the two European Patents relating to *salmonella* metabolic drift mutants and *salmonella* envelope mutants is included in the present Application. Corresponding live marker vaccines for poultry are marketed by the Applicant under the trademark *Salmonella* VAC® T and *Salmonella* VAC® E.

According to an embodiment of the invention at least one well has a coating containing an antibiotic selected from the antibiotics Streptomycin (STRE), Rifampicin (RAM), Erythromycin (ERYD). Streptomycin and Rifampicin are metabolic drift markers of vaccine strains which are cited in EP 0 263 528 B1 and EP 0 642 796 B1. The vaccine strains cited in EP 0 642 796 B1 have an envelope marker which gives it an increased susceptibility relative to Erythromycin. *Salmonella* VAC® T and VAC® E have been developed on the basis of vaccine strains from the two Patents.

According to an embodiment at least one well contains a coating comprising a therapeutically relevant antibiotic for poultry. This makes it possible to check the effectiveness of a therapeutically relevant antibiotic for poultry against a bacterial culture isolated from poultry. In this test an isolated bacterial culture in suspension in a suitable nutritive solution is also dispensed into the well and incubated. Finally, the growth of the bacterial culture is verified with reference to the turbidity. Changes in the susceptibility and the resistance of bacterial isolates towards antibiotics are visible therefrom. This information can be used for determining the state of health of poultry, monitoring resistance and for therapeutic treatment by the vet.

The coating contains an antibiotic which is a therapeutically relevant antibiotic and which is of particular significance or frequently used for the treatment of infectious diseases of poultry. Preferably a plurality of wells with different coatings are provided with a plurality of therapeutically relevant antibiotics. The therapeutic relevance of antibiotics can change over time. New therapeutically relevant antibiotics can appear. The invention includes all antibiotics which at the time and in the future are important for the therapeutic treatment of poultry.

One embodiment comprises at least one well with a coating comprising an antibiotic selected from the antibiotics Ampicillin (AMP), Ceftiofur (CET), Colistin (CST), Enrofloxacin (ENRO), Erythromycin (ERY), Gentamicin (GEN), Lincomycin (LIN), Neomycin (NEO), Oxacillin (OXA), Penicillin G (PEN), Spectinomycin (SPEC), Streptomycin (STRE), Tetracycline (TET), Tiamulin (TIA), Trimethoprim-sulfamethoxazole (T/S). It also refers to antibiotics which have been determined by the Applicant to be currently of high therapeutic relevance for poultry. Ceftiofur is not allowed for the treatment of poultry. Determining the use of Ceftiofur is however interesting for the diagnosis. A plate with a plurality of wells with coatings comprising different antibiotics allows an antibiogram to be established for a bacterial culture isolated from poultry.

If the antibiotic has a predetermined concentration in the coating, a quantitive report on the effectiveness of the antibiotic against the pathogen or the vaccine strain is possible. The test is preferably carried out in accordance with the documentation of the standard procedure criteria, which have been issued by the National Committee for Clinical Laboratory Standards (NCCLS), Wayne, Pa., USA. These are to be found in: National Committee for Clinical Laboratory Standards (2002); Performance Standards for Antimicrobial Disk and Dilution Susceptibility Tests for Bacteria Isolated from Animals; Approved Standard—Second Edition, Document M31-A2, Vol. 22, No. 6, NCCLS, Wayne, Pa., USA.

According to a further embodiment, the coatings of different receivers contain the same antibiotics in different concentrations. This allows quantitative information taken on the MIC as to the effectiveness of an antibiotic against a bacterial culture isolated from poultry. The effectiveness of the antibiotic in-vitro against a specific pathogen can be determined using MIC breakpoints. These are shown corresponding to the clinical categories as susceptible, intermediate and resistant.

Moreover, according to an embodiment, coatings of different receivers contain the antibiotic in a concentration corresponding to the lower breakpoint and the upper breakpoint. The lower breakpoint corresponds to an MIC value which completely prevents sufficient and visible bacterial growth, ie the bacterial isolate is susceptible to the antibiotic. The upper breakpoint corresponds to an MIC value which only partially prevents sufficient and visible bacterial growth and indicates intermediate effectiveness of the antibiotic. Therefore the measurement of MIC values over the upper breakpoint indicates the resistance of the bacterial isolate toward a specific antibiotic. The lower breakpoint and upper breakpoints are respectively taken from the current documentation.

For the embodiment of the invention references are provided in the section of the description devoted to carrying out the test. The wells are coated with the active substance or the antibiotic, such that the desired concentration of active substance is reached by introducing a defined sample amount in the sample.

According to a further embodiment a plurality of wells have the same coating. This allows comparative measurements which increase the reliability of the susceptibility test.

One embodiment comprises at least one well without a coating. This allows a comparative measurement on a bacterial culture, of which the growth is not affected.

One embodiment comprises a plurality of groups of wells, the wells in the groups comprising different coatings and the wells of different groups the same coatings. As a result further comparative measurements are possible.

According to a further embodiment the microtiter plate has 96 wells. This format facilitates working with manual pipettes, in particular. The invention however relates to microtiter plates with a different number of wells, for example 384 or 1536 wells which are in particular suited for processing by robots.

According to an embodiment the microtiter plate is packed in an airtight pouch and as a result the effectiveness of the coatings is guaranteed over a lengthy storage time at room temperature (15-25° C.). According to a further embodiment the pouch also contains a dessicant.

BRIEF DESCRIPTION OF THE SEVERAL VIEWS OF THE DRAWINGS

The invention will be described in more detail hereinafter with reference to the accompanying drawings of an embodiment and an associated table, in which.

DETAILED DESCRIPTION OF THE INVENTION

While this invention may be embodied in many different forms, there are described in detail herein a specific preferred embodiment of the invention. This description is an exemplification of the principles of the invention and is not intended to limit the invention to the particular embodiment illustrated According to FIGS. 1 to 3 a microtiter plate 1 has 96 wells 2. The wells 2 contain coatings 3 which comprise antibiotics. The antibiotics are designated in FIGS. 1 to 3 by acronyms which are associated in Table I with the antibiotics.

Figure 1:
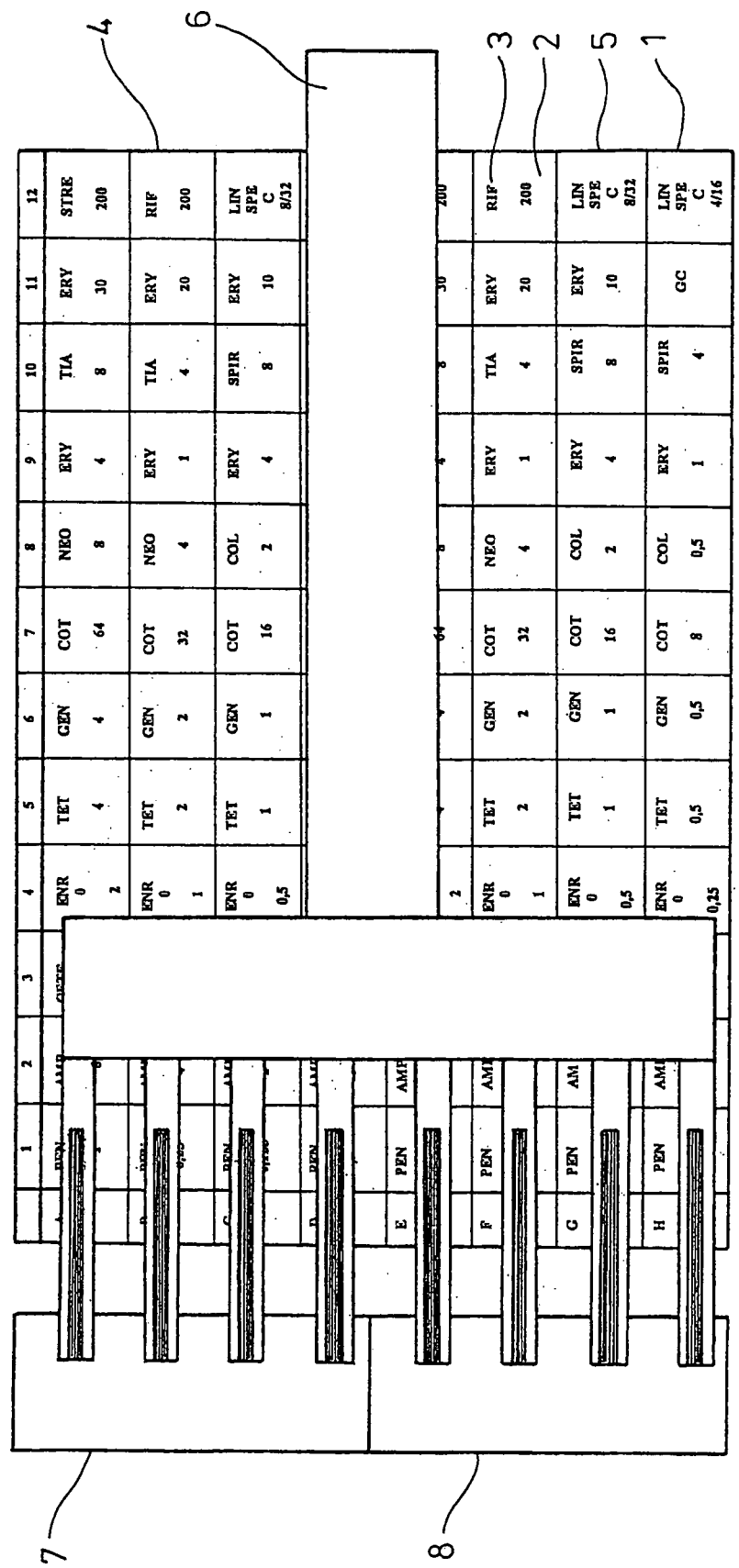
FIGS. 1 to 4 show a roughly diagrammatic top view of a microtiter plate when pipetting a bacterial suspension in a plurality of steps.
Figure 2:
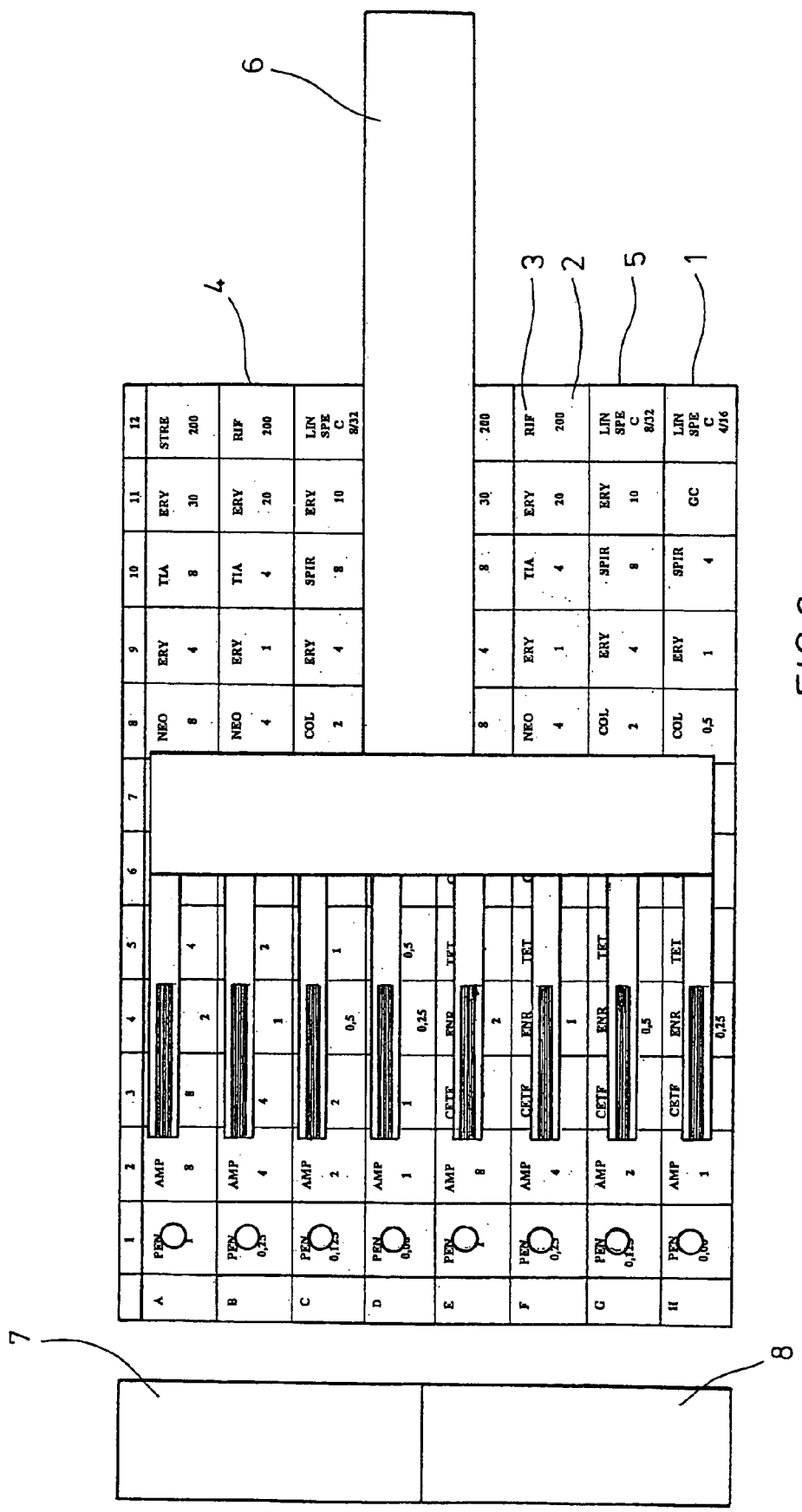
Figure 3:
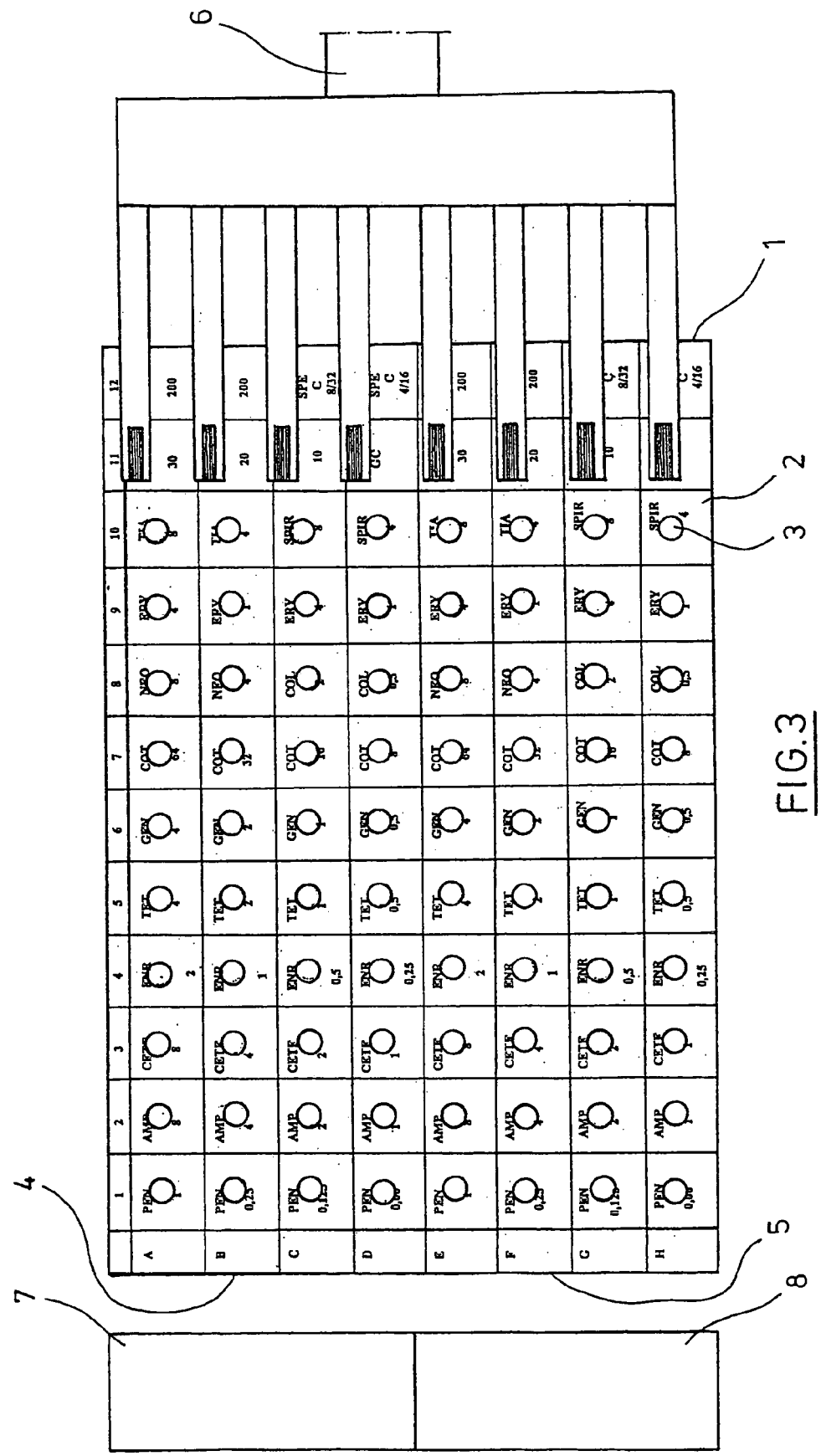
Figure 4:
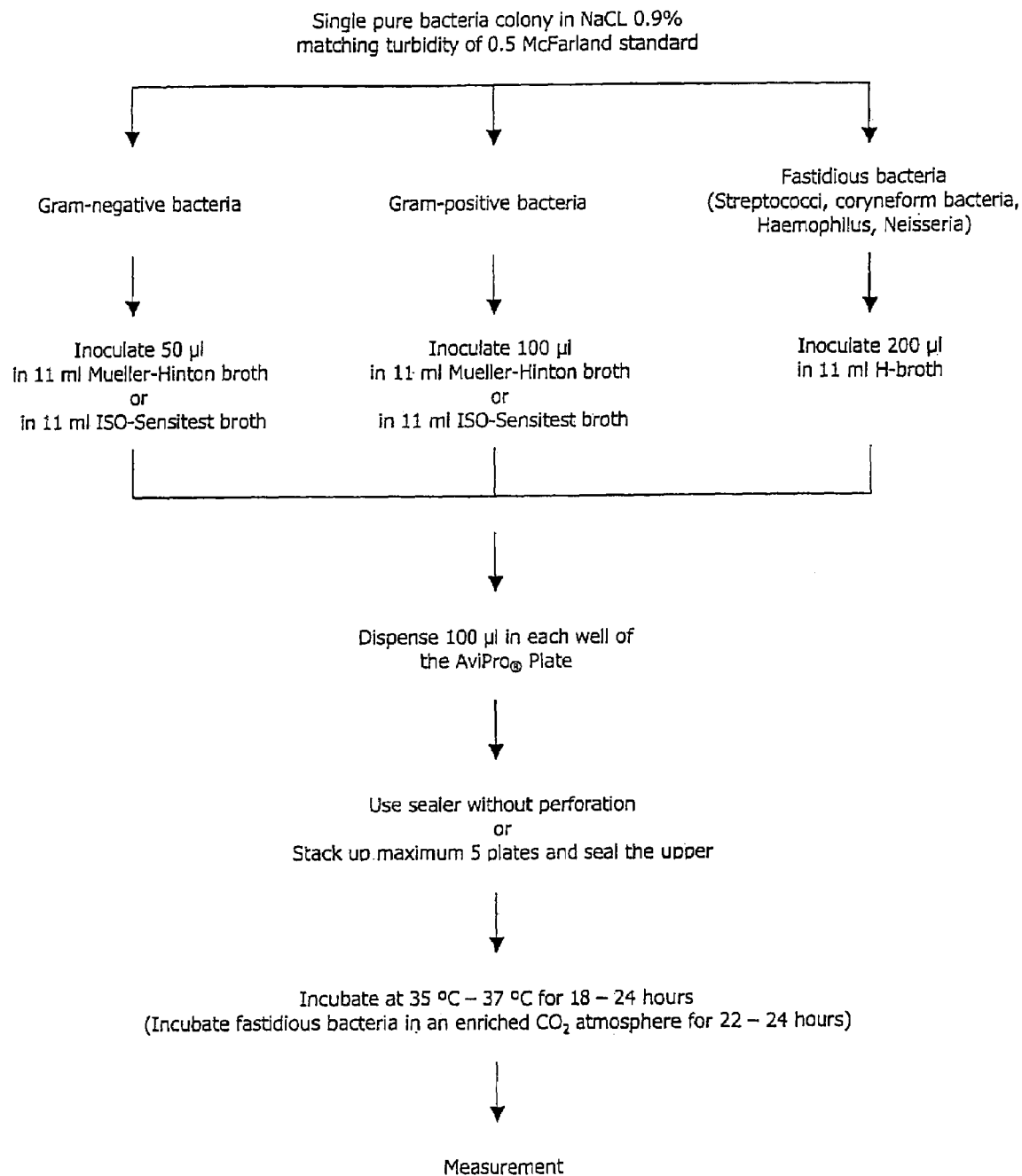

In FIGS. 1 to 3 and in Table I the concentrations of antibiotics in the wells 2 are given in micrograms per millilitre. The concentrations are the masses of the respective antibiotics compared to the volumes of the sample (for example 100 µl) to be pipetted into the wells 2. In Table I the references for the selected concentrations are also shown.

The microtiter plate 1 comprises two groups 4, 5 of wells 2 with identical coatings 3. Group 4 is shown in the drawings in the upper half of the microtiter plate 1 and group 5 in the lower half.

By means of an eight-channel pipette 6 bacterial suspensions 1 and 2 are pipetted from a two channel reservoir 7, 8 into the different wells 2. In FIGS. 1 to 3 different pipetting steps are shown.

Details of how the test is carried out are given in the following description:

Principle of the Test

Determining the susceptibility with the microtiter plate 1 depends on the rehydration of antibiotics by the addition of a standardised bacterial suspension. The result is measured after 18-24 hours incubation at 35-37° C. photometrically with MICRONAUT Skan or another suitable photometer and analysed with MICRONAUT Software or visually read and interpreted.

Microtiter Plate

Each individual microtiter plate 1 is packed in an aluminium pouch together with a dessicant. The test plate contains antibiotics with different concentrations which preferably are used for poultry (see attachment: Table I and the AviPro® plate layout). The microtiter plate 1 allows two susceptibility tests per plate. Each test takes place in up to 48 wells 2 which comprise a palette of 16 antibiotics and a growth control. The wells 2 of rows A to D are designated for test 1 and the wells of rows E to H for test 2. Furthermore there is an adhesive film for sealing the plate.

Suitable Additional Products and Laboratory Materials

Mueller-Hinton broth or ISO-Sensitest broth modified without salt
  H-broth
  NaCl 0.9% pH 5.5 to 6.5 at 37° C.
  1-channel reservoir
  2-channel reservoir
  Multichannel pipette (8- or 12-channel)
  Pipette tips
  MICRONAUT Skan (#L5-120-001) or another suitable photometer
  MICRONAUT Software (#U8-305-001)
  McFarland Standard 0.5
  Blood agar plate
  Incubator 37° C.
  Inoculating loops
  Marker pen (Products with article numbers can be obtained from MERLIN Diagnostika GmbH. MICRONAUT is a trademark of Merlin Diagnostika GmbH.)

Media and Reagents

| Reagent | Composition |
| --- | --- |
| NaCl 0.9% 11 | Sodium Chloride |
| Iso-Sensitest Broth modified (100 tubes @ 11 ml) | Iso-Sensitest Broth Di-Sodium Phosphate |
| H-Broth (100 tubes @ 11 ml) | Hematin, NaOH, Tween 80, Pyridoxal, β-Nicotinamide, Adenine Dinucleotide, Columbia Broth Base, Glucose, Yeast Extract, Neopepton, Agarose Type IIA |
| Mueller-Hinton II Broth | Beef Extract, Acid Casein-Hydrolysate Starch |

Test Procedure

1. Gram Preparation:

Gram-positive bacteria appear blue, gram-negative bacteria red. It is recomended that the gram stain is determined according to standard protocol or the recommendations on the manufacturer's kit.

2. Inoculum Production

Prepare a test tube with 5 ml NaCl 0.9% pH 5.5 to 6.5.
   Remove several individually located colonies of a pure culture which is 18-24 hours old from the blood agar (without additives).
   Homogenise the colonies well in 5 ml NaCl 0.9% until the turbidity corresponds to a McFarland of 0.5.

3. Inoculation in Broth 3.1 Mueller-Hinton broth or modified ISO-Sensitest broth.
      For gram-negative bacteria, 50 µl of the bacterial suspension is pipetted into 11 ml Mueller-Hinton II broth or modified ISO-Sensitest broth and well homogenised.
      For gram-positive bacteria, 100 µl of the bacterial suspension is pipetted into 11 ml Mueller-Hinton II broth or modified ISO-Sensitest broth and well homogenised.

3.2 H-Broth
      For fastidious bacteria, 200 µl of the bacterial suspension is transferred into 11 ml preheated H-Broth and homogenised.

4. Inoculation (Broth-Microdilution)

Remove microtiter plate from the individual packaging max. 30 minutes before inoculation and dispose of the dessicant.
   Label test plate.
   Dispense the prepared suspension according to the plate layout into a 2-channel reservoir.
   The inoculation of the microtiter plate is carried out manually with a multi-channel pipette, 100 µl per well.

5. Sealing and Incubation 5.1 Mueller-Hinton II broth or modified ISO-Sensitest broth
      After inoculating seal the test plates with an unperforated adhesive film or cover with an unused microtiter plate (max. 5 test plates stacked).
      Incubate test plate 18-24 hours at 35-37° C.

5.2 H-Broth
      After inoculating the test plates cover with an unused microtiter plate or with a perforated cover film.
      Incubate test plate 22 to 24 hours at 35 to 37° C. in the incubator with $CO_2$ gassing.

6. Reading

Remove adhesive film.
   Wipe test plate from below.
   Reading of test plate with photometer or visually.

7. Analysis

The bacterial growth is determined using a photometric measurement at a wave length of 620 nm or 690 nm—according to the broth used.
   The result is analysed, interpreted and checked for its plausibility by means of MICRONAUT Software. The growth control must be overgrown (turbid), otherwise the test must be repeated. With visual readout the results should be recorded on a plate layout plan. The test result can be seen on the screen or on the findings report.

8. Interpretation of the Results

Breakpoint Interpretation
   For antibiotics which are tested in four or fewer consecutive concentrations or in non-consecutive concentrations, interpreting categories are determined, namely susceptible, intermediate and resistant, on the basis of low and upper breakpoint MIC values (See attachment: Tables IIA and IIB, Tables IIIA, IIIB, IIIC and IIID and Table IV). The lower breakpoint (LB) is represented by the MIC value which prevents sufficient and visible bacterial growth, ie the bacterial isolate is susceptible to the antibiotic. This upper breakpoint (UB) is represented by the MIC value which partially prevents sufficient and visible bacterial growth and therefore shows intermediate activity relative to the antibiotic. Thus an MIC value over the upper breakpoint (UB) shows a resistance of the bacterial colony relative to the antibiotic. Using MICRONAUT Software, MIC values can be automatically analysed and interpreted for a given bacterial isolate and antibiotic. The test results and the corresponding clinical interpretation including the MIC range can be recommended to the vet for the treatment.

Breakpoint Interpretation of Antibiotics:

| | Visual Readout | | Automatic Readout (OD) | | |
|---|---|---|---|---|---|
| | LB | UB | LB | UB | Clinical Interpretation |
| Bacterial Growth | − | − | <0.1 | <0.1 | Susceptible (S) |
| | + | − | ≧0.1 | <0.1 | Intermediate (I) |
| | + | + | ≧0.1 | ≧0.1 | Resistant (R) |

OD = optical density value analysed with MICRONAUT Software;
LB = lower breakpoint concentration;
UB = upper breakpoint concentration;
+ symbol = well which shows the presence of bacteria;
− symbol = well which shows the absence of bacteria;
[1]intermediate category is not yet established for all antibiotics.
[1]lower breakpoint concentration
[2]upper breakpoint concentration 9. Quality Control Bacterial quality control can be carried out with the following strains:

| Strains | ATCC No. | DSMZ No. |
|---|---|---|
| *Staphylococcus aureus* subsp. *aureus* | ATCC 29213 | DSM 2569 |
| *Escherichia coli* | ATCC 25922 | DSM 1103 |
| *Pseudomonas aeruginosa* | ATCC 27853 | DSM 1117 |
| *Enterococcus faecalis* | ATCC 29212 | DSM 2570 |

ATCC = American Type Culture Collection
DSMZ = Deutsche Sammlung von Mikroorganismen und Zellkulturen GmbH (German Collection of Microorganisms and Cell Cultures GmbH)

REFERENCES

BGVV (Bundesinstitut für gesundheitlichen Verbraucherschutz und Veterinärmedizin—Federal Institute for Public Health and Veterinary Medicine) Table XII/99. Analysis of Inhibition Zone Diameters and Breakpoint Concentrations of Antibiotics Permitted in Veterinary Medicine.

BioSafety in Microbiological and Biomedical Laboratories, HHS Publication No. (CDC) 93-8395, 3$^{rd}$ Edition, May 1993.

National Committee for Clinical Laboratory Standards (2002). Performance standards for antimicrobial disk and dilution susceptibility tests for bacteria isolated from animals; approved standard—second edition. Document M31-A2, Vol. 22, No. 6, NCCLS, Wayne, Pa., USA.

Council Regulation (EEC) No. 2377/90 of 26 Jun. 1990 to lay down a Community Procedure for Establishing Maximum Residue Limits of Veterinary Medicinal Products in Foodstuffs of Animal Origin. Latest Amendment: Commission Regulation (EC) No. 544/2003 of 27 Mar. 2003.

Attachments:

Flow chart of the test procedure

Table I: Details of the antibiotic coatings of the receivers of the same microtiter plate.

Layout of the AviPro microtiter plate

Table II-A: MIC breakpoints and interpretive standards for antimicrobial agents;

Table II-B: Antimicrobial agents which are used as resistance markers to discriminate field strains of *Salmonella enteritidis* (S. E.) and *Salmonella typhimurium* (S. Tm.) from metabolic drift mutants in live vaccines of *Salmonella* Vac E and *Salmonella* Vac T.

Table III-A: MIC range and interpretive result for antibiotics which have been tested on gram-positive reference strains *Staphylococcus aureus* ATCC 29213;

Table III-B: MIC range and interpretive result for antibiotics which have been tested on gram-positive reference strain *Enterococcus faecalis* ATCC 29212.

Table III-C: MIC range and interpretive result for antibiotics which have been tested on gram-negative reference strain *Escherichia coli* ATCC 25922;

Table III-D: MIC range and interpretive result for antibiotics which have been tested on gram-negative test strain *Pseudomonas aeruginosa* ATCC 27853;

Table IV: Rationalisation of interpretive results listed in Tables III-A, III-B, III-C and III-D.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

This completes the description of the preferred and alternate embodiments of the invention. Those skilled in the art may recognize other equivalents to the specific embodiment described herein which equivalents are intended to be encompassed by the claims attached hereto.

TABLE I

Antimicrobial agents pre-coated to AviPro, Plate

| Antimicrobial agents | Agent abbreviation | Reference |
|---|---|---|
| Ampicillin | AMP | EU |
| Ceftiofur | CET | NCCLS |
| Colistin | CST | EU |
| Enrofloxacin | ENRO | EU, NCCLS |
| Erythromycin[1] | ERY | EU, NCCLS |
| Gentamicin | GEN | NCCLS |
| Lincomycin | LIN | EU, NCCLS |
| Neomycin | NEO | EU, NCCLS |
| Oxacillin | OXA | EU |
| Penicillin G | PEN | EU, NCCLS |
| Rifampicin[1] | RAM | Not registered for poultry |

TABLE I-continued

Antimicrobial agents pre-coated to AviPro, Plate

| Antimicrobial agents | Agent abbreviation | Reference |
|---|---|---|
| Spectinomycin | SPEC | EU, NCCLS |
| Streptomycin[1] | STRE | NCCLS |
| Tetracycline | TET | EU, NCCLS |
| Tiamulin | TIA | EU |
| Trimethoprim-sulfamethoxazole | T/S | EU, NCCLS |

EU: refer to Council Regulation (EEC) No. 2377/90;
NCCLS: refer to NCCLS M31-A2 (2002).
[1]Used as resistance marker to discriminate *salmonella* field strains from *salmonelia* metabolic drift mutants in live vaccines of TAD *Salmonella* vac ® E and TAD *Salmonella* vac ® T

AviPro ® Plate layout of antimicrobial agents (µg/ml)

|   |   | 1 | 2 | 3 | 4 | 5 | 6 | 7 | 8 | 9 | 10 | 11 | 12 |
|---|---|---|---|---|---|---|---|---|---|---|---|---|---|
| T E S T 1 | A | PEN 2 | AMP 16 | CET 8 | ENRO 2 | TET 8 | GEN 8 | T/S 4/76 | OXA 2 | ERY 4 | TIA 16 | STRE 200 | RAM 50 |
|   | B | PEN 0.5 | AMP 8 | CET 4 | ENRO 1 | TET 4 | GEN 4 | T/S 2/38 | OXA 1 | ERY 1 | TIA 8 | ERY 30 | SPEC 64 |
|   | C | PEN 0.25 | AMP 4 | CET 2 | ENRO 0.5 | TET 2 | GEN 2 | T/S 1/19 | CST 2 | ERY 0.5 | LIN 4 | ERY 20 | SPEC 32 |
|   | D | PEN 0.12 | AMP 2 | CET 1 | ENRO 0.25 | NEO 8 | GEN 1 | T/S 0.5/9.5 | CST 0.5 | ERY 0.25 | LIN 1 | ERY 10 | Growth Control |
| T E S T 2 | E | PEN 2 | AMP 16 | CET 8 | ENRO 2 | TET 8 | GEN 8 | T/S 4/76 | OXA 2 | ERY 4 | TIA 16 | STRE 200 | RAM 50 |
|   | F | PEN 0.5 | AMP 8 | CET 4 | ENRO 1 | TET 4 | GEN 4 | T/S 2/38 | OXA 1 | ERY 1 | TIA 8 | ERY 30 | SPEC 64 |
|   | G | PEN 0.25 | AMP 4 | CET 2 | ENRO 0.5 | TET 2 | GEN 2 | T/S 1/19 | CST 2 | ERY 0.5 | LIN 4 | ERY 20 | SPEC 32 |
|   | H | PEN 0.12 | AMP 2 | CET 1 | ENRO 0.25 | NEO 8 | GEN 1 | T/S 0.5/9.5 | CST 0.5 | ERY 0.25 | LIN 1 |   | Growth Control |

ERYD = Erythromycin used as resistance marker to discriminate salmonella field strains from salmonella metabolic drift mutants in live vaccines of TAD Salmonella vac ® E and TAD Salmonella vac ® T. Wells exploiting resistance markers are emphasised by lined background.

TABLE II-A

MIC breakpoints and interpretive standards of antimicrobial agents

| Antimicrobial agent Veterinary pathogen | Agent abbreviation | Breakpoint (µg/ml) LB | Breakpoint (µg/ml) UB | Reference |
|---|---|---|---|---|
| Ampicillin[1] | AMP |  |  | NCCLS |
| Enterobacteriaceae |  | 8 | 16 |  |
| Staphylococci |  | 0.25 | — |  |
| Enterococci |  | 8 | — |  |
| Streptococci (not S. pneumoniae) |  | 0.25 | 0.5-4 |  |
| Listeria monocytogenes |  | 2 | — |  |
| Ceftiofur[2] | CET |  |  | NCCLS |
| Bovine (Respiratory Disease) |  | 2 | 4 |  |
| Mannheimia haemolytica |  |  |  |  |
| Pasteurella multocida |  |  |  |  |
| Haemophilus somnus |  |  |  |  |
| Swine (Respiratory Disease) |  | 2 | 4 |  |
| Actinobacillus pleuropneumoniae |  |  |  |  |
| Pasteurella multocida |  |  |  |  |
| Salmonella choleraesuis |  |  |  |  |
| Colistin[1] | CST | 0.5 | 2 | BGVV |
| Enrofloxacin[2] | ENRO |  |  | NCCLS |
| Chicken and turkeys |  | 0.25 | 1 |  |
| Pasteurella multocida |  |  |  |  |
| Escherichia coli |  |  |  |  |
| Erythromycin[1] | ERY |  |  | NCCLS |
| Organisms other than streptococci |  | 0.5 | 1-4 |  |
| Streptococci |  | 0.25 | 0.5 |  |
| Gentamicin[1] | GEN | 4 | 8 | NCCLS |
| Lincomycin[1] | LIN | 1 | 4 | BGVV |

TABLE II-A-continued

MIC breakpoints and interpretive standards of antimicrobial agents

| Antimicrobial agent Veterinary pathogen | Agent abbreviation | Breakpoint (μg/ml) LB | Breakpoint (μg/ml) UB | Reference |
|---|---|---|---|---|
| Neomycin[1] | NEO | 8 | — | BGVV |
| Oxacillin[1] | OXA | | | NCCLS |
| Staphylococci | | 2 | — | |
| Penicillin G[1] | PEN | | | NCCLS |
| Staphylococci | | 0.12 | — | |
| Enterococci | | 8 | — | |
| Listeria monocytogenes | | 2 | — | |
| Spectinomycin[2] | SPEC | | | NCCLS |
| Bovine (Respiratory Disease) Mannheimia haemoloytica Pasteurella multocida Haemophilus somnus | | 32 | 64 | |
| Tetracycline[1] | TET | | | NCCLS |
| Organisms other than streptococci | | 4 | 8 | |
| Tiamulin[2] | TIA | | | NCCLS |
| Swine (Respiratory Disease) Actinobacillus pleuropneumoniae | | 16 | — | |
| Trimethoprim-sulfamethoxazole[1] | T/S | | | NCCLS |
| Organisms other than streptococci | | 2/38 | — | |
| Streptococcus pneumoniae | | 0.5/9.5 | 1/19-2/38 | |

[1]MIC breakpoints and interpretive criteria are based on human rather than animal data.
[2]Minimal inhibitory concentration (MIC) at lower (LB) and upper breakpoint (UB), representing the susceptible and intermediate criteria, respectively, was validated on basis of veterinary indication and taxaspecific bacterial isolate; bacterial growth at MIC values above the UB indicates antimicrobial resistance.

TABLE II-B

Antimicrobial agents used as resistance marker to discriminate field strains of *Salmonella Enteritidis* (S.E.) and *Salmonella Typhimurium* (S.Tm.) from *salmonella* metabolic drift mutants in live vaccines of TAD *Salmonella* vac ® E and TAD *Salmonella* vac ® T

| Antimicrobial agent Veterinary pathogen | Agent abbreviation | Breakpoint (μg/ml) LB | MIC range | Reference[2] |
|---|---|---|---|---|
| Erythromycin[1] Chicken | ERYD | | | LAH |
| S.E. Sm24/Rif12/Ssq (vaccine strain) | | 10 | ≦5 | |
| S.E. Leipzig (field strain) | | 10 | ≧20 | |
| S.Tm. Nal2/Rif9/Rtt (vaccine strain) | | 10 | ≦5 | |
| S.Tm. Moskau 415 (field strain) | | 10 | ≧20 | |
| Rifampicin[1] Chicken | RAM | | | LAH |
| S.E. Sm24/Rif12/Ssq (vaccine strain) | | 50 | >50 | |
| S.E. Leipzig (field strain) | | 50 | <50 | |
| S.Tm. Nal 2/Rif9/Rtt (vaccine strain) | | 50 | >50 | |
| S.Tm. Moskau 415 (field strain) | | 50 | <50 | |
| Streptomycin[1] Chicken | STRE | | | LAH |
| S.E. Sm24/Rif12/Ssq (vaccine strain) | | 200 | >200 | |
| S.E. Leipzig (field strain) | | 200 | <200 | |

[1]For each marker, the minimal inhibitory concentration (MIC) at lower breakpoint (LB) is shown in combination with the MIC range.
[2]MIC values were validated at Lohmann Animal Health (LAH).

TABLE III-A

Range of minimal inhibition concentration (MIC) and interpretive result for antibiotics tested on gram-positive reference strain *Staphylococcus aureus* ATCC 29213

| Antimicrobial agent | Abbreviation | MIC range [μg/ml] | Breakpoint LB + UB | Interpretive result |
|---|---|---|---|---|
| Ceftiofur[1] | CET | 0.25-1 | 2 + 4 | S |
| Colistin[2] | CST | 64 | 0.5 + 2 | R |
| Enrofloxacin[1] | ENRO | 0.03-0.12 | 0.25 + 1 | S |
| Erythromycin[1] | ERY | 0.12-1 | 0.5 + 4 | S/I |
| Gentamicin[1] | GEN | 0.12-1 | 4 + 8 | S |
| Lincomycin[2] | LIN | 0.5-2 | 1 + 4 | S/I |
| Neomycin[2] | NEO | 0.5-2 | 8 | S |
| Oxacillin[1] | OXA | 0.12-0.5 | 2 | S |
| Penicillin G[1] | PEN | 0.25-2 | 0.12 | R |
| Spectinomycin[1] | SPEC | 64-256 | 32 | R |
| Tetracycline[1] | TET | 0.12-1 | 4 + 8 | S |
| Tiamulin[1] | TIA | 0.5-2.0 | 16 | S |
| Trimethoprim-Sulfamethoxazole[1] | T/S | ≦0.5/9.5 | 2/38 | S |

ATCC: American Type Culture Collection (www.atcc.org);
[1]Taken from NCCLS, M31-A2, 2002.
[2]Data validated by MERLIN Diagnostika GmbH.
Rationalisation of interpretive-results is given in FIG. 3.

TABLE III-B

Range of minimal inhibition concentration (MIC) and interpretive result for antibiotics tested on gram-positive reference strain *Enterococcus faecalis* ATCC 29212

| Antimicrobial agent | Abbreviation | MIC range [μg/ml] | Breakpoint LB + UB | Interpretive result |
|---|---|---|---|---|
| Ampicillin[1] | AMP | 0.5-2 | 8 | S |
| Enrofloxacin[1] | ENRO | 0.12-1 | 0.25 + 1 | S/I |
| Erythromycin[1] | ERY | 1-4 | 0.5 + 4 | I |
| Gentamicin[1] | GEN | 4-16 | 4 + 8 | S/I/R |

TABLE III-B-continued

Range of minimal inhibition concentration (MIC) and interpretive result for antibiotics tested on gram-positive reference strain *Enterococcus faecalis* ATCC 29212

| Antimicrobial agent | Abbre-viation | MIC range [μg/ml] | Breakpoint LB + UB | Interpretive result |
|---|---|---|---|---|
| Lincomycin[2] | LIN | 8-32 | 1 + 4 | R |
| Neomycin[2] | NEO | 16-64 | 8 | R |
| Oxacillin[1] | OXA | 8-32 | 2 | R |
| Penicillin G[1] | PEN | 1-4 | 8 | S |
| Spectinomycin[1] | SPEC | 64-256 | 32 | R |
| Tetracycline[1] | TET | 8-32 | 4 + 8 | I/R |
| Trimethoprim-Sulfamethoxazole[1] | T/S | ≦0.5/9.5 | 2/38 | S |

For further explanation see table III-A.

TABLE III-C

Range of minimal inhibition concentration (MIC) and interpretive result for antibiotics tested on gram-negative reference strain *Escherichia coli* ATCC 25922

| Antimicrobial agent | Abbre-viation | MIC range [μg/ml] | Breakpoint LB + UB | Interpretive result |
|---|---|---|---|---|
| Ampicillin[1] | AMP | 2-8 | 8 + 16 | S |
| Ceftiofur[1] | CET | 0.25-1 | 2 + 4 | S |
| Colistin[2] | CST | ≦0.5 | 0.5 + 2 | S |
| Enrofloxacin[1] | ENRO | 0.008-0.03 | 0.25 + 1 | S |
| Gentamicin[1] | GEN | 0.25-1 | 4 + 8 | S |
| Neomycin[2] | NEO | 0.5-2 | 8 | S |
| Spectinomycin[1] | SPEC | 8-64 | 32 | S/R |

TABLE III-C-continued

Range of minimal inhibition concentration (MIC) and interpretive result for antibiotics tested on gram-negative reference strain *Escherichia coli* ATCC 25922

| Antimicrobial agent | Abbre-viation | MIC range [μg/ml] | Breakpoint LB + UB | Interpretive result |
|---|---|---|---|---|
| Tetracycline[1] | TET | 0.5-2 | 4 + 8 | S |
| Trimethoprim-Sulfamethoxazole[1] | T/S | ≦0.5/9.5 | 2/38 | S |

For further explanation see table III-A.

TABLE III-D

Range of minimal inhibition concentration (MIC) and interpretive result for antibiotics tested on gram-negative reference strain *Pseudomonas aeruginosa* ATCC 27853

| Antimicrobial agent | Abbre-viation | MIC range [μg/ml] | Breakpoint LB + UB | Interpretive result |
|---|---|---|---|---|
| Ceftiofur[1] | CET | 16-64 | 2 + 4 | R |
| Colistin[2] | CST | 0.5-2 | 0.5 + 2 | S/I |
| Enrofloxacin[1] | ENRO | 1-4 | 0.25 + 1 | I/R |
| Gentamicin[1] | GEN | 0.5-2 | 4 + 8 | S |
| Lincomycin[2] | LIN | 32 | 1 + 4 | R |
| Tetracycline[1] | TET | 8-32 | 4 + 8 | R |
| Trimethoprim-Sulfamethoxazole[1] | T/S | 8/152-32/608 | 2/38 | R |

For further explanation see table III-A.

TABLE IV

Rationalisation of interpretive results listed in tables III-A, III-B, III-C and III-D

| Interpretive result | Rationalisation |
|---|---|
| S | The MIC range of the control strain is below or equivalent to the lower breakpoint concentration. |
| I | The MIC range of the control strain is above the lower breakpoint concentration but below or equivalent to the upper breakpoint concentration. |
| R | The MIC range of the control strain is above the upper breakpoint concentration. |
| S/I | The MIC range of the control strain is below, equivalent or above the lower breakpoint concentration but below or equivalent to the upper breakpoint concentration. |
| I/R | The MIC range of the control strain is above the lower breakpoint concentration but below or equivalent or above the upper breakpoint concentration. |
| S/I/R | The MIC range of the control strain is below or equivalent to the lower breakpoint concentration, or the MIC range of the control strain is above the lower breakpoint concentration but below or equivalent to the upper breakpoint concentration, or the MIC range of the control strain is above the upper breakpoint concentration. |

What is claimed is:

1. A method for discrimination between pathogenic field strains and vaccine strains of bacterial pathogens in poultry, the method comprising the steps of:
   providing a microtiter plate comprising a plurality of wells, at least one of the plurality of wells having a coating containing an antibiotic of a marker of a vaccine strain used for the vaccination of poultry;
   dispensing a pure bacterial culture suspended in a nutritive solution into the at least one of the plurality of wells;
   incubating the microtiter plate;
   measuring the growth of the bacteria; and
   determining whether the pure bacterial culture is a pathogenic field strain or a vaccine strain.

2. The method of claim 1, wherein at least one of the plurality of wells has a coating containing an antibiotic of a marker of a salmonella vaccine strain.

3. The method of claim 1, wherein at least one of the plurality of wells has a coating containing an antibiotic, the antibiotic being selected from Streptomycin, Rifampicin, and Erythromycin.

4. The method of claims 1, wherein at least one of the plurality of wells has a coating containing a therapeutically relevant antibiotic for poultry.

5. The method of claim 4, wherein at least one of the plurality of wells has a coating containing an antibiotic selected from Ampicillin, Ceftiofur, Colistin, Enrofloxacin, Erythromycin, Gentamicin, Lincomycin, Neomycin, Oxabillin, Penicillin G, Spectinomycin, Streptomycin, Tetracycline, Tiamulin, Trimetho-primsulfamethoxazole.

6. The method of claim 5, wherein the plurality of wells comprise wells having a coating of an antibiotic having a concentration, the concentration of the antibiotic in each well being different.

7. The method of claim 6, the concentration of the antibiotic in one well being the lower breakpoint of the minimum inhibitory concentration and the concentration of the antibiotic in another well being the upper breakpoint of the minimum inhibitory concentration 8. The method of claims 1, in which the coatings of different wells contain different antibiotics.

9. The method of claim 8, further comprising establishing an antibiogram for a bacterial culture isolated from poultry.

10. The method of claim 1, in which some of the plurality of wells have the same coating.

11. The method of claim 1, wherein at least one of the plurality of wells has no coating.

12. The method of claim 1, wherein the plurality of wells form a plurality of groups of wells, the wells in the groups comprising different coatings and the wells of different groups comprising the same coatings.

13. The method of claim 1, wherein the microtiter plate comprises 96 wells.

14. The method of claim 1, wherein the microtiter plate is stored in an airtight pouch before use.

15. The method of claim 14, wherein the pouch contains a dessicant.

16. The method of claim 1, further comprising measuring the growth of the bacteria by measuring turbidity of the suspension.

17. The method of claim 16, wherein the turbidity of the suspension is measured by a photometer.

18. The method of claim 1, wherein a vaccine strain and a pathogenic strain have different susceptibilities to an antibiotic as measured by the growth of the bacteria.

* * * * *